Figure 1:
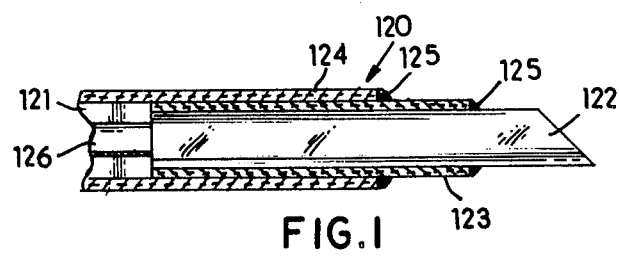

United States Patent [19]

Collins

[11] 4,089,223
[45] May 16, 1978

[54] DEVICE AND METHOD OF OBTAINING A SAMPLE OF LIQUID

[76] Inventor: William J. Collins, 7005 Madison St., Merrillville, Ind. 46410

[21] Appl. No.: 682,576

[22] Filed: May 3, 1976

Related U.S. Application Data

[62] Division of Ser. No. 563,590, Mar. 31, 1975, Pat. No. 4,002,072.

[51] Int. Cl.² ............................................. G01N 1/12
[52] U.S. Cl. ............................................. 73/425.4 R
[58] Field of Search .......... 73/425.4 R, 425.6, DIG. 9

[56] References Cited

U.S. PATENT DOCUMENTS

| 3,455,164 | 7/1969 | Boyle | 73/DIG. 9 |
|---|---|---|---|
| 3,646,816 | 3/1972 | Hance | 73/DIG. 9 |
| 3,791,219 | 2/1974 | Falk | 73/DIG. 9 |
| 3,859,857 | 1/1975 | Falk | 73/DIG. 9 |

*Primary Examiner*—S. Clement Swisher

[57] ABSTRACT

The invention involves providing a unique device and method of obtaining a sample of liquid, such as molten metal, preferably from a stream thereof. The device embodies wall structure forming a chamber and an entrance passage or tubular formation having a coating of material applied to at least a portion of the passage for conditioning the liquid or metal as it flows into the chamber.

10 Claims, 1 Drawing Figure

U.S. Patent    May 16, 1978    4,089,223

DEVICE AND METHOD OF OBTAINING A SAMPLE OF LIQUID

BACKGROUND OF INVENTION

This application is a Division of my copending application Ser. No. 563,590 filed Mar. 31, 1975 now U.S. Pat. No. 4,002,072.

The various devices disclosed in the subject application preferably comprise, among other things, a pair of half sections which form a primary chamber for receiving molten metal and tubular means or tube, preferably of Pyrex or other suitable heat resistant material, which has an inner extremity held in relation to the primary chamber by the half sections and an outer extremity provided with an entrance or inlet for initially receiving molten metal for flow through the tubular means into the primary chamber.

In view of the foregoing, one of the important objects of the subject invention is to provide a device comprising a receiving means preferably composed of a pair of half sections forming a tubular formation or passage and a primary chamber for receiving a sample of molten metal, including tubular means having an inner extremity disposed in relation to the tubular formation and an outer extremity provided with an entrance for initially receiving molten metal for flow through the tubular means into the chamber, and coating means lining at least a portion of said formation or passage for conditioning the metal as it flows into the chamber.

Additional specific objects of the invention reside in providing a device with a deoxidizing means which is applied as a liner or layer to at least one of the passages communicating with the primary chamber.

A specific object is to provide a unique method of deoxidizing the sample obtained.

Additional objects and advantages of the invention reside in providing a device which is efficient, durable, comprised of a minimum number of components which can be economically manufactured and assembled on a production basis and which can be readily disassembled or broken apart after use to obtain a sample.

Other objects will become apparent after the description hereinafter set forth is considered in conjunction with the drawings annexed hereto:

In the drawings:

FIG. 1 is a partial longitudinal sectional view of a device embodying the invention.

FIG. 1 depicts a device generally designated 120. This device comprises a pair of half sections, preferably constructed of powdered metal which is inherently porous and have channel portions 121 (one shown) forming a tubular formation, a tubular means or tube 122 of Pyrex or equivalent inexpensive material, a sleeve 123 and a casing 124. The sleeve and casing are preferably made of pasteboard and square or rectangular in cross-section. It should be noted that the sleeve extends outwardly from the casing 124 and serves to support the extended portion or extremity of the tube 122. Cement 125 may serve to seal the outer end of the casing to the sleeve and the outer end of the sleeve to the tubular means. The device 120 affords a setup whereby the molten metal will flow directly into a cylindrical passage formed by the channel portions and this passage has a diameter somewhat less than the internal diameter of the tube 122. It should be further noted that the inner ends of the tubular means and sleeve abut the ends of the channel portions of the half sections and that the latter comprises wall structure forming a chamber (not shown) which receives the liquid or molten metal from the passage, tubular formation or tube 122.

Attention is directed to the important fact that the internal surfaces defining the passage or opening formed by the channel portions 121 of the sections are provided with a layer or coating 126 of means, such as aluminum or some other pyrophoric substance which is sprayed onto the surfaces to constitute an element for deoxidizing the metal flowing through the passage, as distinguished from the other forms of deoxidizing means described in the subject application. Obviously, a layer or coating of aluminum, adherent or equivalent material could be sprayed or otherwise applied to the inner surface of the tube 122, or to any of the tubes, passages or chambers located between an outer entrance and a primary chamber. For example, the internal surface of the tube 58, entrance 62' or chamber 62 shown in FIG. 5 in the parent application could be provided with a layer of aluminum of sufficient thickness in lieu of the means 51, in which event, the inner end of the tube 58 would more or less only engage the conical surface or surfaces 61 of the chamber 62 and that the coating can be applied as stated with respect to FIG. 8 of said application.

Having thus described my invention or inventions, it is obvious that various modifications may be made in the same without departing from the spirit of the invention and, therefore, I do not wish to be understood as limiting myself to the exact forms, constructions, arrangements, and combinations of the parts herein shown and described.

I claim:

1. A device for obtaining a sample of molten metal comprising wall structure forming a primary chamber and a tubular passage leading to said chamber, and said passage being provided with a sprayed layer of material for conditioning the molten metal prior to its flow into the chamber.

2. A method of obtaining a sample of molten metal which comprises inserting a device having a chamber and a passage leading to the chamber into a mass of molten metal whereby the metal will be caused to flow successively into the passage and chamber, and subjecting the molten metal to a layer of adherent material applied to the internal surfaces of the passage for conditioning at least some of the molten metal prior to its flow into the chamber.

3. A subassembly of a device for obtaining a sample of molten material, said subassembly comprising wall structure forming a chamber and an internal porous area forming a tubular passage communicating with said chamber, and fusible means substantially filling the pores of said area for conditioning the material when it flows through the passage into said chamber for solidification.

4. A subassembly of a device for obtaining a sample of molten material, said subassembly comprising wall structure forming a chamber and a tubular passage communicating with said chamber, said passage having an internal porous area, and means substantially filling the pores of said area.

5. The subassembly defined in claim 4, in which said tubular passage has variable internal cross-dimensions.

6. A subassembly of a device for obtaining a sample of molten material, said subassembly comprising structure forming a chamber and tubular means through which such material may be caused to flow into said chamber, and said tubular means having at least a portion of its internal area coated by a fusible means for conditioning the material as it flows into said chamber for solidification.

7. A device for obtaining a sample of molten material, said device comprising an elongated casing, wall structure disposed in said casing and forming a chamber and a tubular formation having an internal porous area, tubular means having an inner extremity secured in said casing in relation to said tubular formation and an extremity for receiving such material for flow into said chamber via said tubular formation, and fusible means substantially filling said porous area for conditioning the material prior to its flow into said chamber for solidification.

8. A device for obtaining a sample of molten material, said device comprising walls forming a chamber, a pair of tubular structures forming a passage through which such material may be caused to flow into said chamber, means coating an internal area of one of said tubular structures for fusion into the material as it flows therethrough, and means for maintaining said walls and tubular structures assembled.

9. A device for obtaining a sample of molten material, said device comprising a casing, structure disposed in said casing and forming a chamber and a tubular entrance thereto, tubular means secured in said casing and having an inner end disposed in relation to said entrance, and coating bonded to at least an internal area of said entrance for conditioning the material as it flows toward said chamber for solidification.

10. A method of obtaining a sample of molten material which comprises inserting a device having a chamber and a tubular passage leading to said chamber into a mass of such material to cause the latter to flow into said chamber, and subjecting the material to a coating of fusible means lining said passage for conditioning the material as it flows to said chamber for solidification.

* * * * *